(12) United States Patent  
Harris (10) Patent No.: US 7,093,508 B2  
(45) Date of Patent: Aug. 22, 2006

(54) SAMPLING APPARATUS FOR MATERIAL COLLECTION

(75) Inventor: Joel Steven Harris, 6073 Valley Field Crescent, Gloucester, Ontario (CA) K1C5P3

(73) Assignee: Joel Steven Harris, Orleans (CA)

( * ) Notice: Subject to any disclaimer, the term of this patent is extended or adjusted under 35 U.S.C. 154(b) by 551 days.

(21) Appl. No.: 10/116,072

(22) Filed: Apr. 5, 2002

(65) Prior Publication Data

US 2002/0164272 A1    Nov. 7, 2002

(30) Foreign Application Priority Data

May 2, 2001    (CA) ................................. 2345911

(51) Int. Cl.
*G01N 1/04* (2006.01)

(52) U.S. Cl. .............. 73/864.44; 73/864; 73/864.41; 83/919

(58) Field of Classification Search ............ 422/99, 422/100; 73/864, 864.13, 864.41, 864.44, 73/864.45; 600/564, 567
See application file for complete search history.

(56) References Cited

U.S. PATENT DOCUMENTS

| 3,683,892 | A | * | 8/1972 | Harris | 600/567 |
| 3,783,998 | A | * | 1/1974 | Brush et al. | 206/364 |
| 3,786,811 | A | * | 1/1974 | Holbrook | 604/218 |
| 4,461,305 | A | * | 7/1984 | Cibley | 600/567 |
| 4,733,671 | A | * | 3/1988 | Mehl | 600/567 |
| 4,991,600 | A | * | 2/1991 | Taylor | 600/567 |
| 5,184,625 | A | * | 2/1993 | Cottone et al. | 600/564 |
| 5,456,125 | A | * | 10/1995 | Gagne | 73/864.44 |
| 5,691,206 | A | * | 11/1997 | Pawliszyn | 436/178 |
| 5,696,330 | A | * | 12/1997 | Heinonen | 73/864.13 |
| 6,352,673 | B1 | * | 3/2002 | Rainin et al. | 422/100 |
| 6,565,728 | B1 | * | 5/2003 | Kozulic | 204/606 |
| 6,702,990 | B1 | * | 3/2004 | Camacho et al. | 422/100 |

* cited by examiner

*Primary Examiner*—Jill Warden
*Assistant Examiner*—Paul Hyun (57) ABSTRACT

An apparatus to collect a sample of material has a handle with a tubular sample sleeve extending from an end of the handle. The end of the sleeve distal from the handle forms a cutting edge circumscribing a circular sampling region. A plunger slides reciprocally within the tubular sample sleeve between a retracted position and an expulsion position. A user cuts a sample from a source material by engaging contact between the cutting edge of the tubular sample sleeve and the source material. The sample cut from the source is lodged within the tubular sample sleeve. Actuation of the plunger from the retracted position toward the expulsion position displacing the sample from the sleeve.

4 Claims, 9 Drawing Sheets

SAMPLING APPARATUS FOR MATERIAL COLLECTION

BACKGROUND OF THE INVENTION

1. Field of Invention

The invention relates to the field of micro-sampling for the collection of in situ material such as human tissue, field samples for related environmental examination, crime scene sampling, or other related materials or material prepared on a substrate and then sampled such as dried blood on a blood card. Sampling regimes are designed to extract a micro-sample from a larger source sample material. The micro-samples extracted may be chemically analyzed for the purposes of DNA analysis, nondestructively analyzed by placement on the appropriate spectra generating sample stage or observed under microscopic conditions.

2. Description of Prior Art

Sampling devices are conventionally used to extract samples from materials such as paper, cloth, wood, tissues and the like. In one arrangement, a sampling device has a tubular sleeve forming a cutting edge at one end. A sample is obtained by advancing the sleeve into the sample source. The sleeve may then be gently rocked to separate the sample from the source, thereby retaining the sample in the cutting sleeve. The sample is then removed from the cutting sleeve using a second tool in the form of a pick or probe. In one prior art arrangement, the cutting sleeve provides an auxiliary opening extending along the length of the sleeve to facilitate removal of the sample. The extracted sample may then be placed in a receptacle, or may be mounted on a support.

Removal of sample from the cutting sleeve in either method as described above, presents a number of problems that may affect the integrity of the sample. Moreover, sample handling may present potential health hazards to the technician working with the sample. The process of picking a sample from the cutting sleeve is inefficient and time consuming. The conventional methods described above expose technicians to unnecessary health risks through the handling of sharp cutting instruments to extricate the retained sample material from the cutting sleeve. The sample material can also be partially lost, dropped or contaminated consequently requiring further sampling or the inability to do further sampling.

SUMMARY OF INVENTION

The present invention is a sample collection apparatus comprising an elongate handle, a tubular sample sleeve extending from one end of the handle having a cutting edge at an end of the tubular sample sleeve distal from the handle. The sampling device has a plunger reciprocally operable to displace a sample from the tubular sample sleeve. In one embodiment, an end of the plunger is linked to an actuator that axially displaces the plunger within the handle of the apparatus. The actuator controls the movement of the plunger through a linkage joining the plunger to the actuator. A sample is cut from a source by the cutting edge of the tubular sample sleeve. A sample is collected from a source by excision from the source as the tubular sample sleeve is urged into contact with the source. The sample is received within the lumen of the tubular sample sleeve. Once removed from the source, the sampling device can be used to transport the sample that is thereby lodged within the lumen of the tubular sample sleeve. The sample is expelled from the tubular sample sleeve by the plunger which is displaceable axially through the lumen of the tubular sample sleeve. The plunger can expel the entire sample at once, or incrementally to permit sectioning the sample into smaller portions as it is partially expelled from the sleeve. Another embodiment for actuating the plunger is comprised of a spring cover that biases the plunger in the retracted position until actuation for expulsion of a sample.

The present invention allows the user to withdraw a sample from a source and retain it within the tubular sample sleeve until needed. Suitable sample sources for this invention include soft materials such as cloth, paper, wood, films, gels, plant, animal and human tissues, and other sources capable of being cut by a surgical steel cutting edge. Ejection of the sample in increments allows for small portions of the sample to be segmented from the whole of the sample without removal of the entire sample from the cutting sleeve. Using this technique reduces likelihood for inadvertent or accidental cutting and repeated extraction from the cutting sleeve. The plunger eliminates the need for direct handling of the sample and reduces the likelihood of potential contamination that may require re-sampling of the source. This reduces the amount of manipulation to be performed by the technician who collects the sample, and reduces potential risks for contamination of the sample or contact between the user and the sample.

In this invention, the cutting sleeve serves as a cutting tool and as a storage receptacle to retain the sample. The plunger enables quick, safe and clean removal of the sample from the cutting sleeve.

Preferably, the sampling device is made from materials that are stable to heat of sterilization. The device can also be used as a disposable tool. The sampling device is particularly suited to be readily transported either alone or as part of a kit for the collection and transportation of samples.

DESCRIPTION OF THE PREFERRED EMBODIMENT

Figure 1:
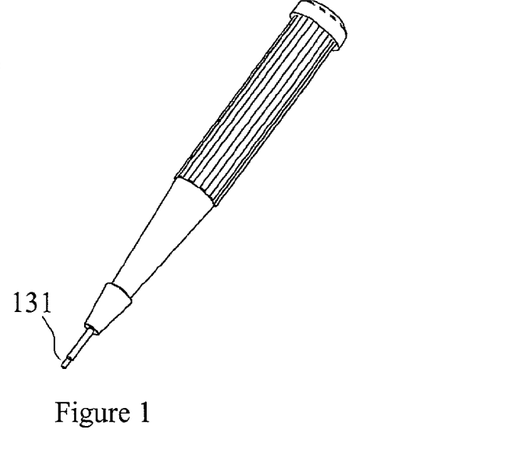
FIG. 1 is an elevation view showing a preferred embodiment of a sample collection apparatus constructed in accordance with the principles of the invention shown with the sample plunger in the expulsion position.
Figure 1A:
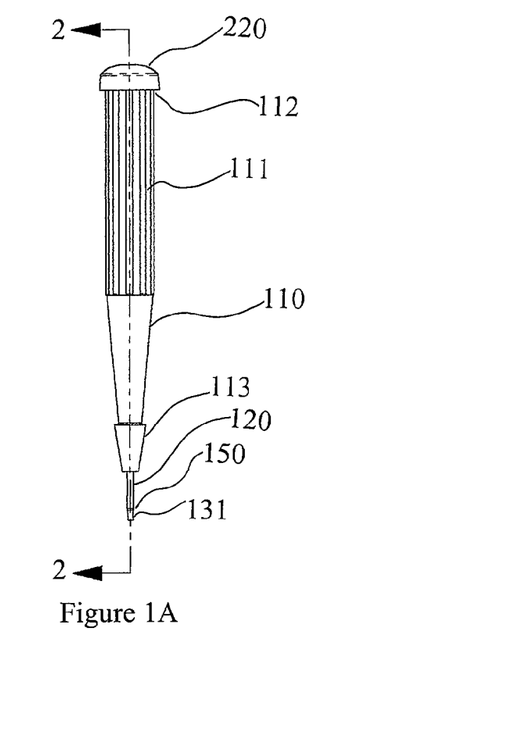
FIG. 1A is an elevation view of FIG. 1 along section axis 2—2.

Referring to FIGS. 1 and 1A, a preferred embodiment of a sample collection device constructed in accordance with the principles of the invention is shown. A handle 110 has a tubular sample sleeve 120 extending from one end of the handle 110 indicated by 113. The exterior surface of the handle may include a plurality of ridges 111 to provide a better gripping surface for the user. There is a plunger 131 shown here in an expulsion position, where the plunger 131 extends past cutting edge 150 of tubular sample sleeve 120.

Figure 2:
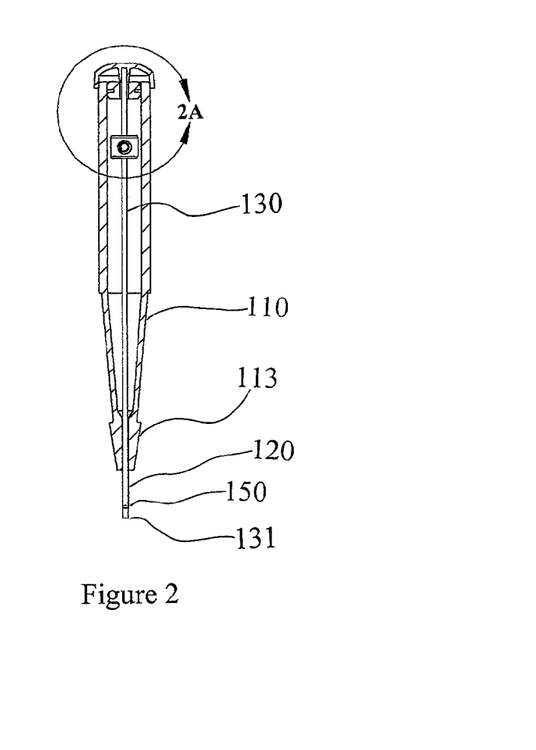
FIG. 2 is a cross-sectional view of the apparatus of FIG. 1A taken along section line 2—2 of FIG. 1A in the expulsion position.
Figure 3:
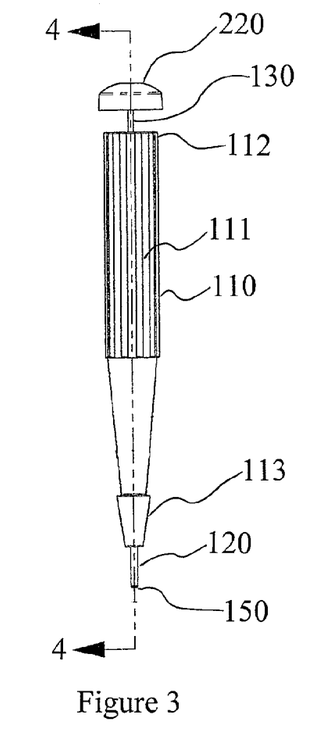
FIG. 3 is an elevation view showing the apparatus in FIG. 1 in the retracted position.
Figure 4:
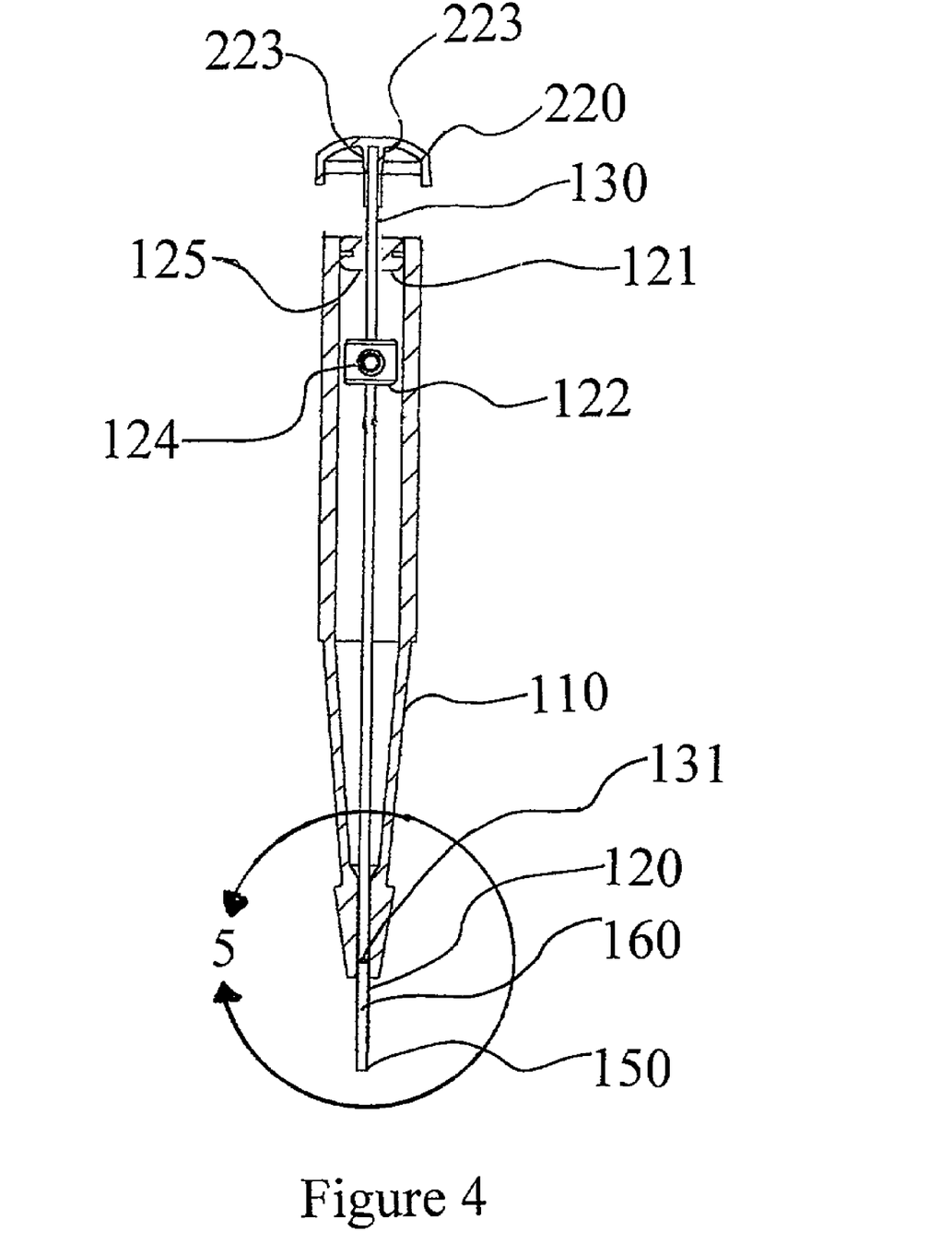
FIG. 4 is a cross-sectional view of the apparatus taken along section line 4—4 of FIG. 3 in the retracted position.

FIG. 2 and shows a longitudinal cross-section of the device taken along cutting line 2—2 of FIG. 1A. A linkage 130 connects plunger 131 to an actuator, shown here as cover 220, which axially reciprocates plunger 131 through the lumen of sleeve 120 between an expulsion position, as shown in FIGS. 1, 1A and 2, and a retracted position as shown in FIGS. 3 and 4. The retracted position has plunger 131 positioned within the apparatus and preferably within tubular sample sleeve 120, whereas the expulsion position has plunger 131 positioned outside of tubular sample sleeve 120, extended past cutting edge 150.

The cover 220 can have an inner diameter that is equal to or slightly larger than the outer diameter of the first end 112 of the handle 110. The cover 220 is used to activate the plunger 131 and can form a seal with the first end 112 of the handle 110 when not in use. The plunger 131 can be attached to the cover by various means, such as by linkage 130 within a flange 223 as shown in FIG. 2A.

Figure 2A:
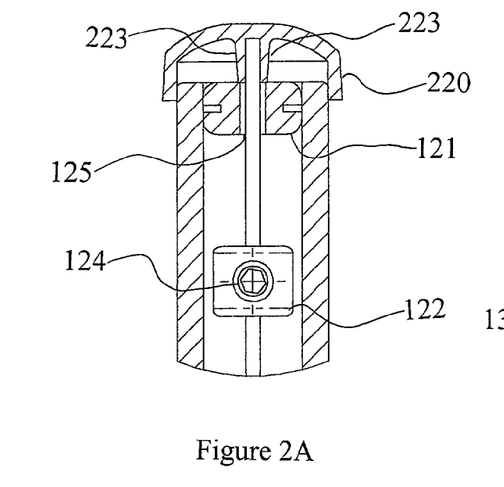
FIG. 2A is an exploded view of the removable cap and plunger in the expulsion position on FIG. 2.

FIG. 2A is an exploded view of the cover 220 and cover assembly to linkage 130 in FIG. 2.

In a preferred embodiment, a grommet 121 and stopper assembly can be used for retaining the cover 220, linkage 130 and plunger 131 attached to handle 110, and particularly for setting the retracted position for plunger 131 within tubular sample sleeve 120. A grommet 121 can be disposed at the upper interior portion of the handle 112, opposite the end from which sleeve 120 extends. Grommet 121 is preferably made from a material that can be compressed for insertion within the handle but which retains its elasticity and returns to its original size. For example, grommet 121 can be made from soft rubber. A stopper 122 can be attached to linkage 130. When cover 220 is removed from handle 110, plunger 131 slides with tubular sample sleeve 120 until stopper 122 contacts grommet 121, thus defining the range of reciprocal motion of plunger 131 in the retracted position.

Figure 5:
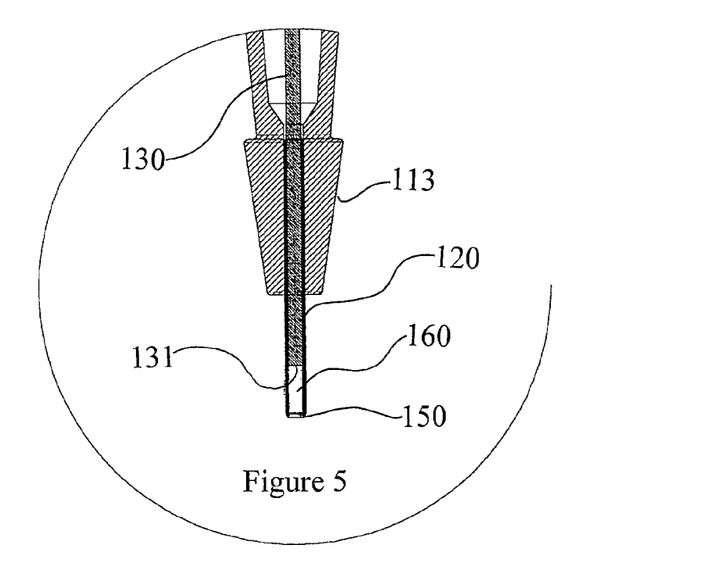
FIG. 5 shows an enlarged, partial cross section of the apparatus bounded by circle 5 shown in FIG. 4.

Referring to FIGS. 3, 4, and 5, the cover 220 mounts onto handle 110 detachably, allowing plunger 131 to slide within the length of the tubular sample sleeve 120. The plunger 131 is moved between the retracted and expulsion positions by movement of cover 220 and linkage 130, which communicates the axial displacement to plunger 131. When cover 220 is fitted on handle 110, plunger 131 extends outwardly through tubular sample sleeve 120 and past cutting edge 150 to the expulsion position. As cover 220 is removed from handle 110, plunger 131 withdraws into tubular sample sleeve 120 to the retracted position.

As shown in FIGS. 2 and 4, linkage 130 is mounted to the inside of cover 220 and is held in place by flanges 223. Linkage 130 slides freely within grommet 121 through aperture 125 of grommet 121. Stopper 122 is held in place as shown in this embodiment with a hexagonal screw 124. When cover 220 is removed from handle 110, linage 130 and plunger 131 can be slid axially through handle 110 away from cutting edge 150 of sleeve 120. When stopper 122 contacts grommet 121, cover 220 can no longer be displaced from handle 110, and plunger 131 can no longer move further away from cutting edge 150. FIG. 4 shows cover 220 raised from first end 112 so that plunger 131 is located within tubular sample sleeve 120 for removing a sample from a source. Stopper 122 is preferably positioned so as to prevent plunger 131 from being dislodged from within tubular sample sleeve 120.

Figure 8:
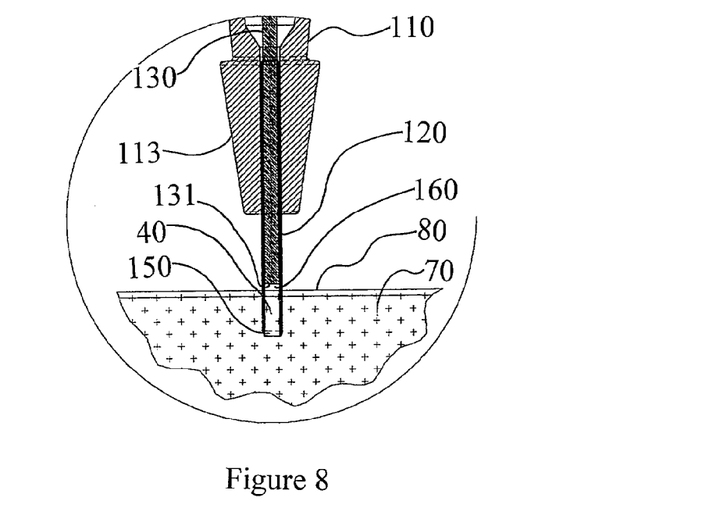
FIG. 8 is an enlarged cross-sectional view of the sample cutting and collection portion of the apparatus defined by circle 5 in FIG. 4 where the apparatus is being used to take a sample of a substrate as is shown in FIG. 6.

As shown in FIG. 4, 5 and 8, when plunger 131 is in the retracted position, there is a chamber 160 created within tubular sample sleeve 120 so as to permit entry of a sample 40 cut by cutting edge 150 into tubular sample sleeve 120 from a sample source 70.

Figure 6:
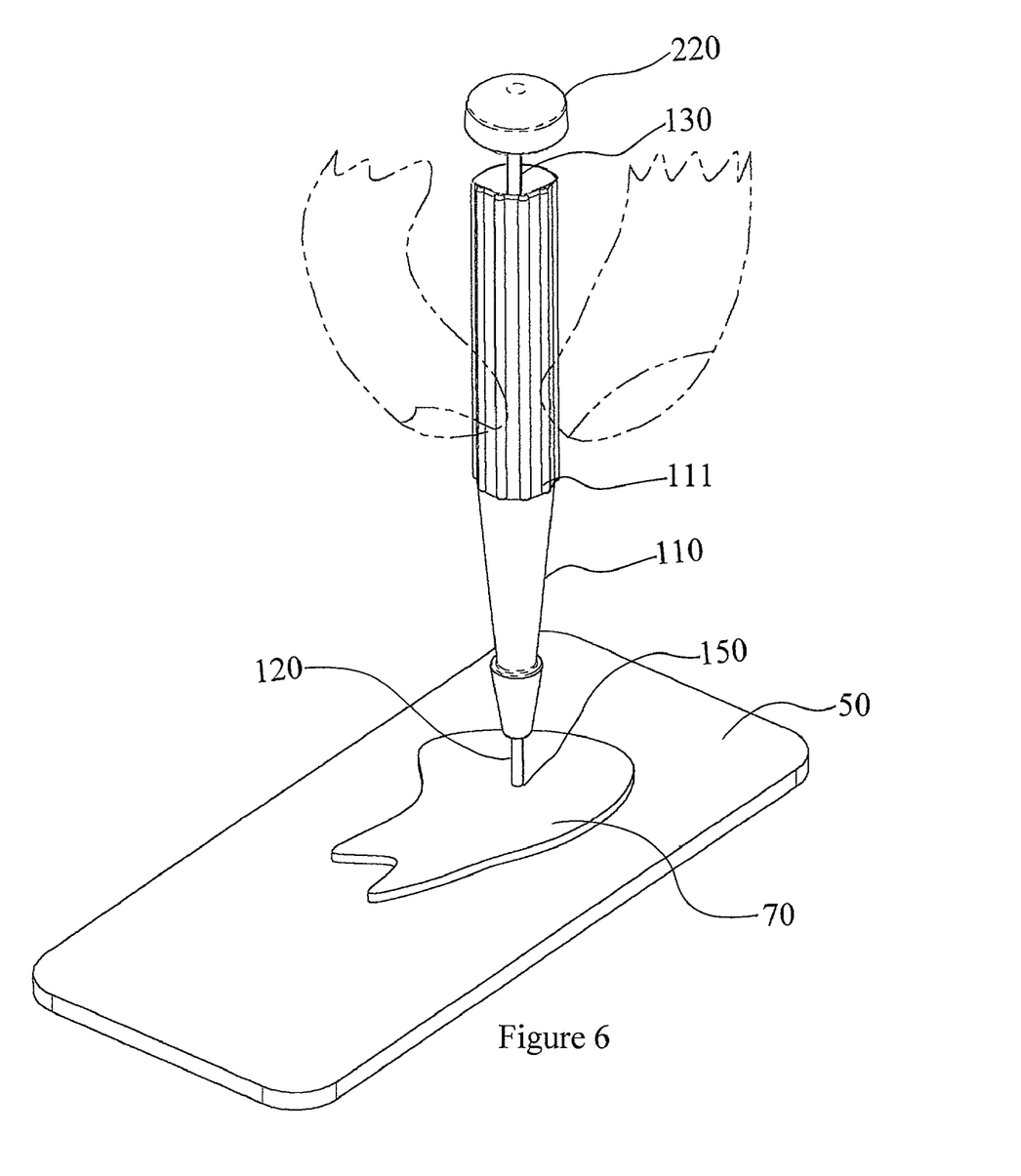
FIG. 6 shows a perspective view of the sample collection apparatus of FIG. 1 being operated to collect a sample from a source on a self-healing, inert mat.

FIG. 5 shows a longitudinal cross-sectional view of the area in FIG. 4 bounded by circle 5. Plunger 131 is shown retracted within tubular sample sleeve 120 creating a chamber 160 within the tubular sample sleeve 120 that will be filled by a sample that is to be removed from a source. FIG. 6 shows use of the coring device in association with source 70, which is being cut using self-healing inert support 50. Tubular sample sleeve 120 has perforated source 70 at its surface. The user is holding handle 110, and has displaced cover 220, so as to withdraw plunger 131 into the barrel of tubular sample sleeve 120. Grommet 121 and topper 122 are not shown in this embodiment. Cutting of a sample 40 using inert support 50 is preferred where the source 70 being cut is the material to be analyzed, for example, cloth, wood, or tissue.

Figure 7:
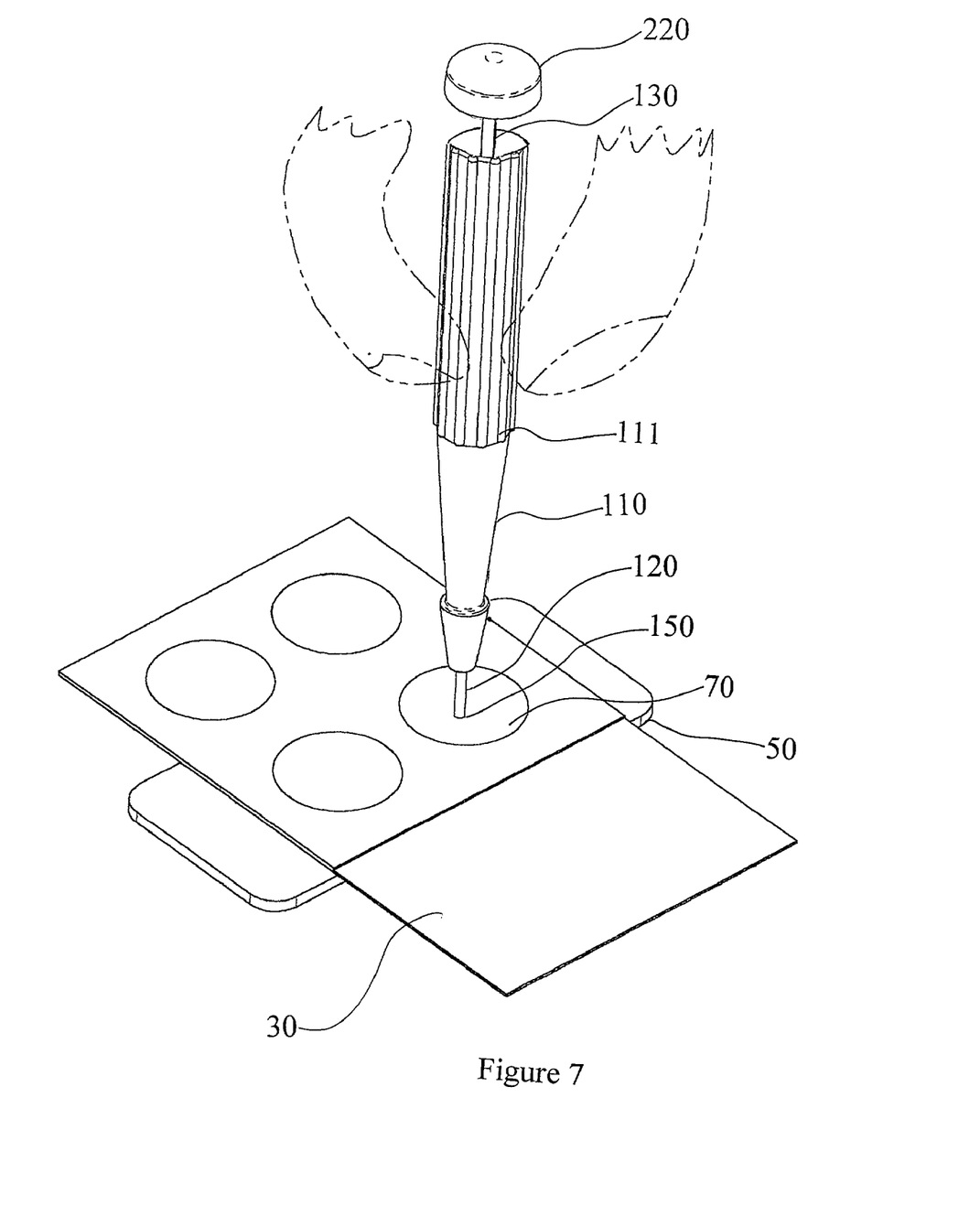
FIG. 7 shows a perspective view of the sample collection apparatus of FIG. 1 in use to collect a sample from a piece of blotting paper, on a self-healing, inert mat.

FIG. 7 shows a similar configuration as in FIG. 6, except the source 70 is absorbed on blotting paper 30 or other absorptive material that has the sample absorbed on its surface and within the microstructure of the absorptive material, for example, blood blotted on paper.

FIG. 8 shows the same view as FIG. 5 except cutting edge 150 and tubular sample sleeve 120 have penetrated surface 80 of source 70. Cutting edge 150 is located within source 70, while plunger 130 is retracted from surface 80 of source 70. Chamber 160 is practically filled by sample 40 from source 70.

Figure 9:
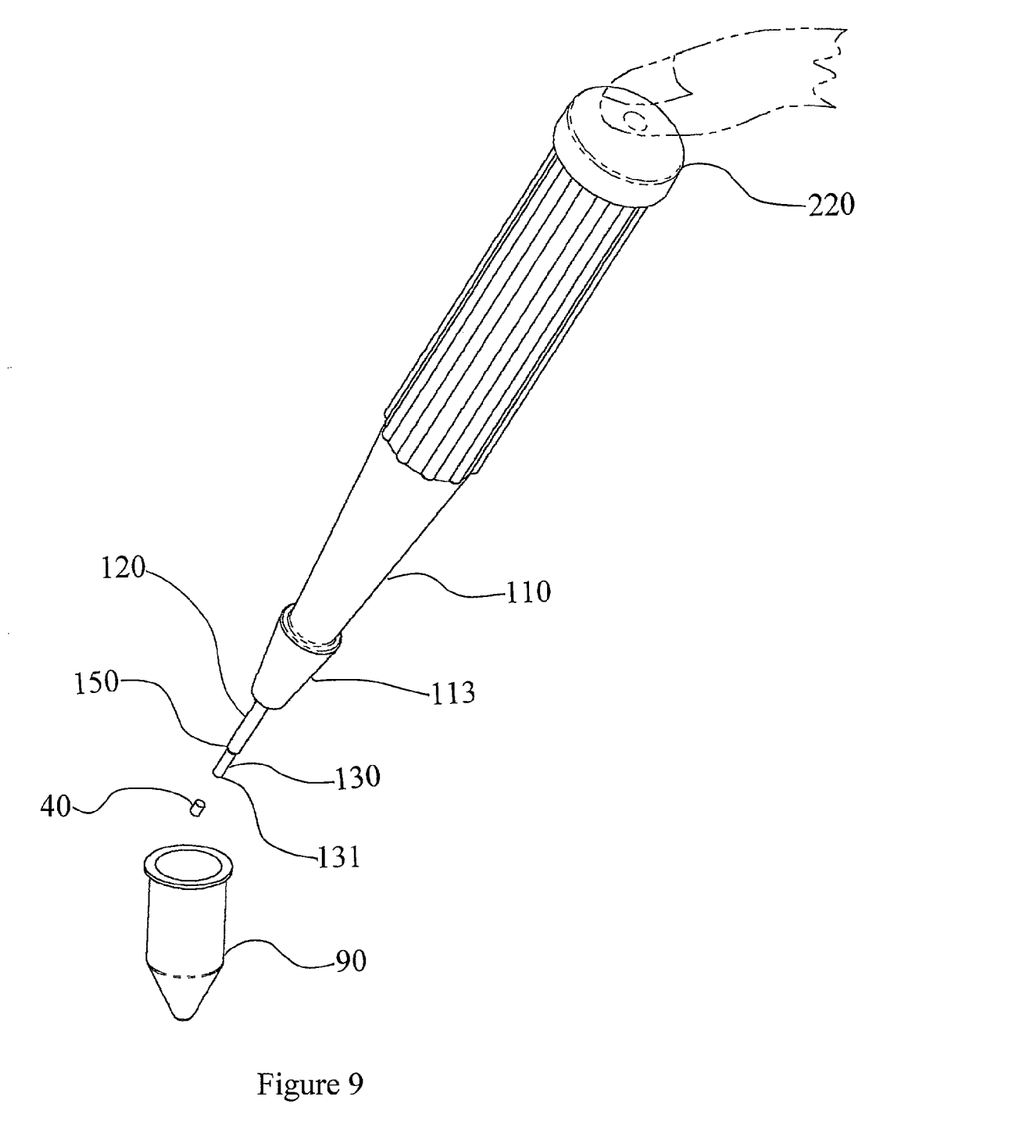
FIG. 9 shows a perspective view of the sample collection apparatus of FIG. 1, where a sample is being ejected into a receptacle.
Figure 10:
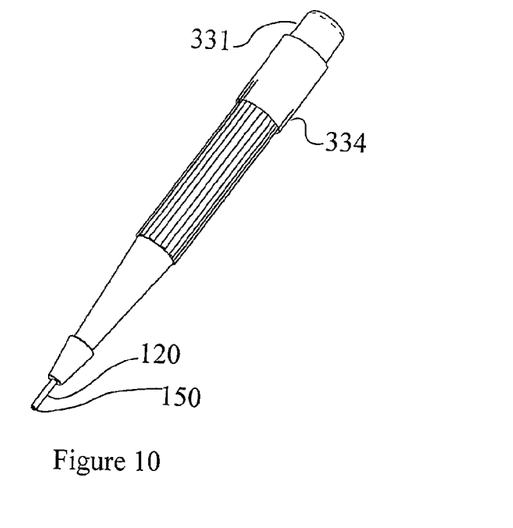
FIG. 10 is an elevation view of another preferred embodiment of an sample collection apparatus constructed in accordance with the principles of the invention shown with the plunger in the retracted position.
Figure 10A:
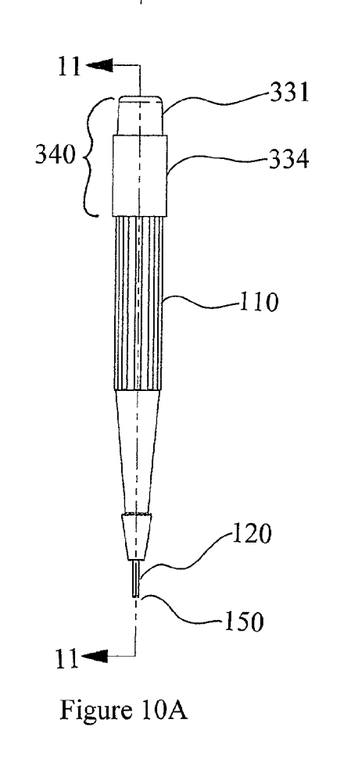
FIG. 10A is an elevation view of FIG. 10 along section axis 11—11.

FIG. 9 shows the ejection of sampled material 40 into vial collecting receptacle 90. The user repositions cover 220 onto handle 110 which in turn slides plunger 131 through tubular sample sleeve 120 and past cutting edge 150, forcing the expulsion of sample 40.

In another preferred embodiment, as shown in FIGS. 10, 10A, 11, 12 and 13, a spring ejection cover 340 has a cap 334 that engages the first end 112 of handle 110, and a spring and shaft assembly that is mounted to spring ejection cover 340 within cap 334. The spring ejection cover 340 is comprised of an actuator 331, a spring 337 and an enclosure 338 for the spring 337, a shaft 336 and the plunger 131. The shaft 336 is mounted to the actuator 331 at one end, and is buttressed against spring 337 at the other. The linkage 130 is mounted on the end of the shaft 336 that is buttressed against spring 337. Linkage 130 can lie within the coils of spring 337 as shown by these drawings. As actuator 331 is pressed into cover 330 by shaft 336, which also compresses spring 337 and displaces plunger 130 axially. The spring 337 is also buttressed against the enclosure 338 that holds the spring and shaft assembly against flange 333. When the actuator 331 is no longer pressed, the spring 337 returns the actuator 331 and the shaft 336 to the retracted position, moving plunger 130 back to its first position, within annular cutting sleeve 120. Cap 334 can have an inside diameter that is slightly larger than the outside diameter of handle 110 and can be fitted onto the handle 110 accordingly.

The present embodiments of the invention allow the sample 40 to be ejected from cutting sleeve 120 in its entirety or in increments. One can also eject sample 40 into a collection vial 90 without working sample 40 free of tubular sample sleeve 120. The controlled ejection of sample 40 from the tubular sample sleeve 120 allows for small portions of sample 40 to be cut away from the whole sample by way of scalpel without removing all of sample 40 from tubular sample sleeve 120.

The device can also be sued to sample source 70 resting on an inert support 50, such as a self-healing cutting mat. Because the device is rotated with downward pressure, it cuts the source 70 with the cutting edge 150 of tubular sample sleeve 120, into inert support 50, so that inert support 50 forces sample 40 into tubular sample sleeve 120. The collected sample 40 is then retained in the tubular sample sleeve 120 until such time when it is displaced therefrom by actuation of the plunger 131.

Figure 11:
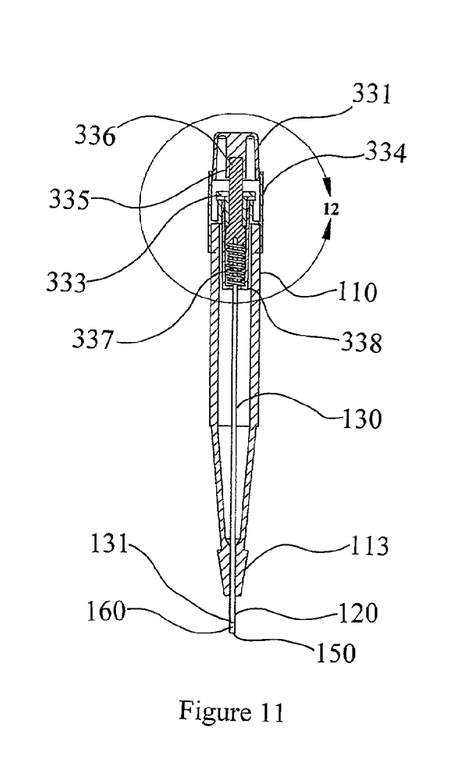
FIG. 11 is a cross section taken along section line 11—11 of FIG. 10A.
Figure 12:
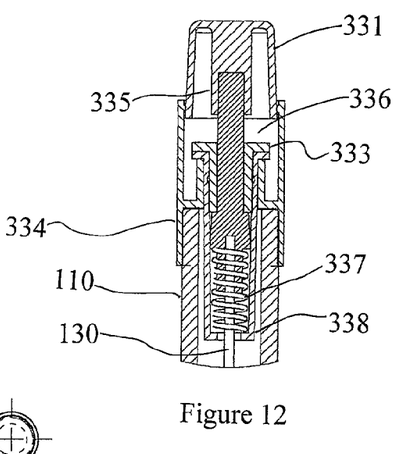
FIG. 12 Shows an enlarged partial cross section of the apparatus comprising the area encompassed in FIG. 11 by circle 12.

FIG. 11 shows actuator 331 mounted within cover 330, which in turn is mounted on handle 110. FIG. 12 shows a magnified view of the cross section of spring ejection cover 340. Attached to actuator 331 is shaft 336, which is mounted to actuator 331 at flange 335. When actuator 331 is pressed by the user, flange 335 contacts opposing flange 333 within the cover, thus limiting the motion of actuator 331. As actuator 331 is pressed, shaft 336 slides within opposing flange 333 and spring 337 contracts against enclosure 338. As shaft 336 moves axially within handle 110, linkage 130 is similarly engaged and also moves axially through handle 110. When actuator 331 is pressed inward onto cap 334, shaft 336 moves axially towards tubular sample sleeve 120, and in turn forces linkage 130 to move plunger 131 through tubular sample sleeve 120 towards cutting edge 150. When actuator 331 is moved through its complete range of motion, and spring 337 is at its most compressed point, linkage 130 should extend past cutting tip 150 outside of tubular sample sleeve 120 in the expulsion position.

Figure 13:
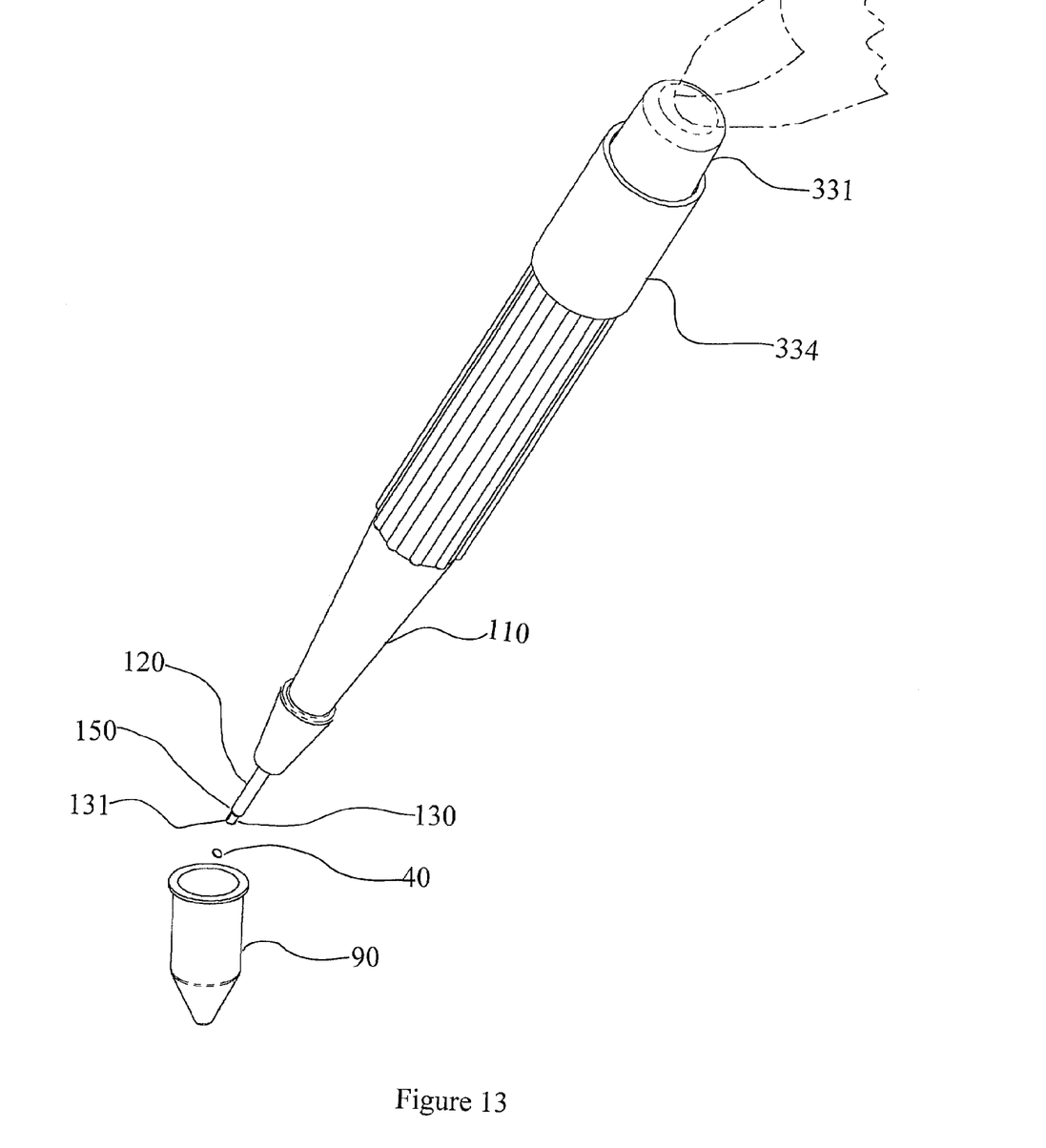
FIG. 13 shows a perspective view of the apparatus on FIG. 11 where a sample is being ejected into a receptacle, the plunger being in the expulsion position.
Figure 14:
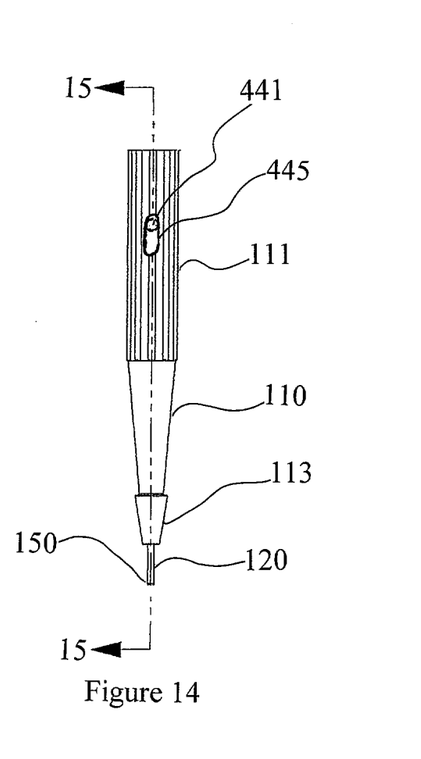
FIG. 14 shows an elevation view of another embodiment of a sampling device constructed in accordance with the principles of the invention, having a slide actuator for expelling a sample from within the device, the plunger being in the retracted position.

FIG. 13 shows sample 40 being ejected into collecting vial 90 by the pressing of actuator 331. This embodiment of the invention can be used as shown in FIGS. 6 and 7, for example.

Referring to FIGS. 14, 15, 16 and 17, an embodiment of the invention is shown where plunger 131 is movable between a first position where plunger 131 is within the apparatus (the retracted position) and where plunger 131 extends past tubular sample sleeve 120 and cutting edge 150 (the expulsion position). The plunger 131 is moved between these two positions using sliding arm 441, the actuator in this embodiment, which attached to stopper 442 on linkage 130, sliding arm 441 extending through opening 445 on handle 110. Opening 445 is preferably located at a position approximately central among plurality of ridges 111 used for gripping the apparatus, and has a length in the axial direction of handle 110 that is sufficient to allow sliding arm 441 to move plunger 131 between the retracted and expulsion positions. Stopper 442 is mounted to linkage 130 along its length, preferably at the end of linkage 130 opposite the plunger 131. Sliding arm 441 moves between a first position and a second position within opening 445, the first position of the sliding arm 441 corresponding to the retracted position of plunger 131, and the second position of the sliding arm 441 corresponding to the expulsion position of plunger 131.

Figure 15:
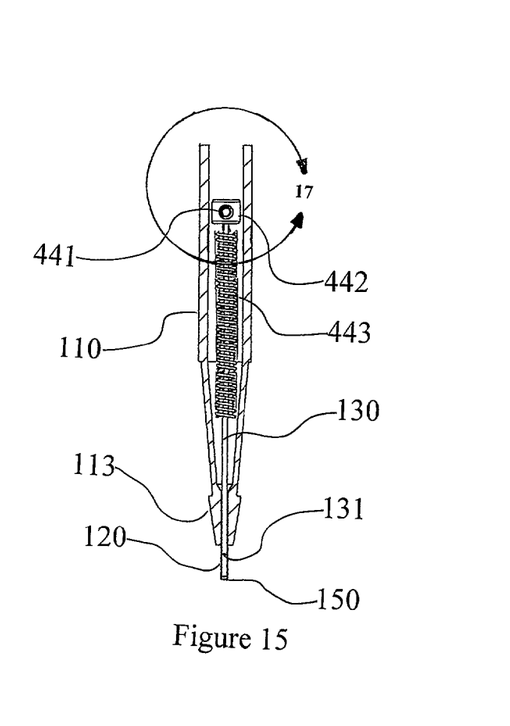
FIG. 15 shows a longitudinal cross-sectional view of the sampling device taken along cutting line 15—15 of FIG. 14, shown with the plunger in the retracted position.
Figure 16:
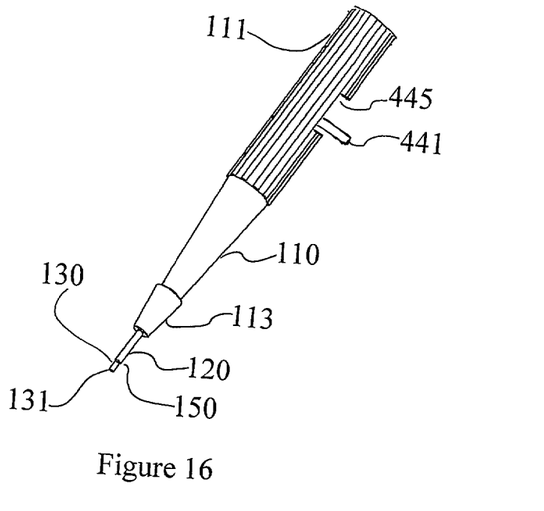
FIG. 16 shows a plan view of the embodiment of the sampling and collecting device of FIG. 14, where the device has been rotated about its longitudinal axis by 90 degrees, and with the plunger and the slide actuator shown in the expulsion position.
Figure 17:
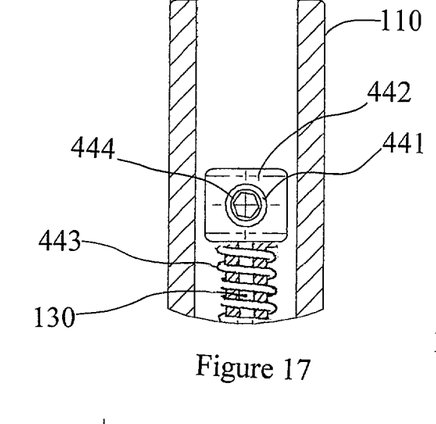
FIG. 17 is an enlarged view of the portion of the FIG. 15 defined by circle 17.

Referring more particularly to FIGS. 15 and 17, sliding arm 441 is mounted to a stopper 442, which in turn is mounted to linkage 130. Biased against stopper 442 is spring 443, which is mounted between tubular sample sleeve 120 and stopper 442, around linkage 130. Spring 443 biases plunger 131 and sliding arm 441 in the retracted position until moved into the expulsion position by a user seeking to expel a sample. Spring 443 also keeps plunger 131 in alignment with tubular sample sleeve 120. The plunger 131 can be moved to positions between the first and second position for gradual expulsion of a sample from within the tubular sample sleeve 120.

I claim:
1. A method for sampling a circular shaped sample area from a sample source, the method comprising the steps of:
  I) providing a sampling device, the device comprising:
    an elongated, hollow handle configured to be grasped by the fingers;
    a tubular sample sleeve depending from an end of said handle wherein the end of said sample sleeve that is not connected to said handle forms a circular cutting blade;
    a spring ejection cover capping the end of said handle opposite said sample sleeve;
    a shaft depending from said spring ejection cover, said shaft in contact with a spring housed within an enclosure and connected to a linkage that connects to a plunger, said plunger being slidably movable within said sample sleeve between a retracted position that defines a lumen bounded by the tip of said plunger and said cutting blade and an expulsion position defined by said plunger being actuated past the cutting blade;
  II) placing a sample material on a cutting support;
  III) choosing a target area of the sample;
  IV) maintaining said plunger in said retracted position;
  V) holding the handle of the sampling device between the fingers of one hand;
  VI) using the other hand to hold the sample to restrict the movement of the sample;

VII) positioning the cutting blade of the sampling device perpendicularly above said target area;
VIII) bringing said handle downward until said cutting blade is in contact with the surface of the sample source;
IX) applying downward pressure while rotating said handle to cut a core of said sample material;
X) bringing the entire surface of the cutting blade into contact with the cutting support thereby urging the sample into the lumen of the sample sleeve;
XI) lifting the sampling device from the sample material;
XII) depressing the spring ejection cover to actuate the plunger from said retracted position towards the cutting blade;
XIII) actuating the plunger beyond the cutting blade to fully eject the sample; and
XIV) releasing the spring ejection cover thereby allowing the plunger to return to the retracted position.

2. The method as set forth in claim 1 wherein the movement of the plunger is configured to be effected in small increments.

3. The method as set forth in claim 2 wherein the tubular sample sleeve is made of surgical steel.

4. The method as set forth in claim 2 wherein the exterior surface of the handle includes a plurality of ridges to provide a better gripping surface.

* * * * *